United States Patent [19]
Gleason

[11] Patent Number: 6,121,291
[45] Date of Patent: Sep. 19, 2000

[54] PAROXETINE IN THE TREATMENT OF DEPRESSION ASSOCIATED WITH WITHDRAWAL FROM HEROIN ABUSE AND POST-TRAUMATIC STRESS DISORDER

[75] Inventor: Maurice Gleason, Newbury, United Kingdom

[73] Assignee: SmithKline Beecham plc, Brentford, United Kingdom

[21] Appl. No.: 09/142,990

[22] PCT Filed: Mar. 17, 1997

[86] PCT No.: PCT/EP97/01353

§ 371 Date: Feb. 11, 1999

§ 102(e) Date: Feb. 11, 1999

[87] PCT Pub. No.: WO97/34602

PCT Pub. Date: Sep. 25, 1997

[30] Foreign Application Priority Data

Mar. 20, 1996 [GB] United Kingdom .................... 9605828

[51] Int. Cl.[7] .................................................. A61K 31/445
[52] U.S. Cl. ............................................................ 514/321
[58] Field of Search ............................................... 514/321

[56] References Cited

U.S. PATENT DOCUMENTS 4,007,196 2/1977 Christensen et al. .
5,789,449 8/1998 Norden ................... 514/651

FOREIGN PATENT DOCUMENTS 0 223 403 5/1987 European Pat. Off. .
WO95/16448 6/1995 WIPO .

OTHER PUBLICATIONS

Nemeroff, Biological Abstracts, abstract No. 1994:231203.
Duboff, Biological Abstracts, abstract No. 1994:120027, 1993.
Caley et al, Biological Abstracts, abstract No. 1994:23694, 1993.
Claghorn, Biological Abstracts, abstract No. 1992:239102.

*Primary Examiner*—William R. A. Jarvis
*Attorney, Agent, or Firm*—Wayne J. Dustman; William T. King; Charles M. Kinzing

[57] ABSTRACT

This invention relates to the use of paroxetine or a pharmaceutically acceptable salt thereof for the treatment of post-traumatic stress disorder and depression associated with withdrawal from heroin abuse.

2 Claims, No Drawings

PAROXETINE IN THE TREATMENT OF DEPRESSION ASSOCIATED WITH WITHDRAWAL FROM HEROIN ABUSE AND POST-TRAUMATIC STRESS DISORDER

This application is a 371 of PCT/EP97/01353, filed Mar. 17,1997.

The present invention relates to the treatment and/or prevention of specific types of depression.

U.S. Pat. No. 4,007,196 discloses the compound, (−)-trans-4-(4'-fluorophenyl)-3-(3'4'-methylenedioxyphenoxymethyl) piperidine, and, in Example 2, a process by which it can be prepared. The compound, which is referred to herein by its common name, paroxetine, is described in the patent as an inhibitor of 5-hydroxytryptamine uptake and, therefore, is of use in the treatment of depression in general.

It has now been surprisingly discovered that paroxetine has particularly effective therapeutic utility for treating and/or preventing specific types of depression.

Accordingly, the present invention provides a method for treating and/or preventing the following depression sub-types: adolescent, bipolar, elderly, major, minor, moderate, recurrent, refractory, severe unipolar, dysthymia, post natal, double depression, post psychotic, post viral, bereavement, primary, secondary, post traumatic stress disorder and depression associated with withdrawal from substances of abuse such as alcohol, nicotine, cocaine, heroin, benzodiazepines, in human or non-human animals, which method comprises administering an effective, non-toxic amount of paroxetine or a pharmaceutically acceptable salt thereof, to human or non-human animals in need thereof.

The present invention also provides the use of paroxetine or a pharmaceutically acceptable salt thereof in the manufacture of a medicament for use in the treatment of and/or prevention of the following depression sub-types: adolescent, bipolar, elderly, major, minor, moderate, recurrent, refractory, severe unipolar, dysthymia, post natal, double depression, post psychotic, post viral, bereavement, primary, secondary, post traumatic stress disorder and depression associated with withdrawal from substances of abuse such as alcohol, nicotine, cocaine, heroin, benzodiazepines,.

A preferred salt of paroxetine is the hydrochloride, particularly in crystalline form, such as the hemi-hydrate.

A medicament, for use in the treatment and/or prevention of the following depression sub-types: adolescent, bipolar, elderly, major, minor, moderate, recurrent, refractory, severe unipolar, dysthymia, post natal, double depression, post psychotic, post viral, bereavement, primary, secondary, post traumatic stress disorder and depression associated with withdrawal from substances of abuse such as alcohol, nicotine, cocaine, heroin, benzodiazepines, may be prepared by admixture of paroxetine or a pharmaceutically acceptable salt thereof with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use as an agent in the treatment and/or prevention of the following depression sub-types: adolescent, bipolar, elderly, major, minor, moderate, recurrent, refractory, severe unipolar, dysthymia, post natal, double depression, post psychotic, post viral, bereavement, primary, secondary, post traumatic stress disorder and depression associated with withdrawal from substances of abuse such as alcohol, nicotine, cocaine, heroin, benzodiazepines.

The suitable dosage range for paroxetine or a pharmaceutically acceptable salt depends on the severity of the disorders and on the condition of the patient. It will also depend, inter alia, upon the relation of potency to absorbability and the frequency and route of administration.

Paroxetine or a pharmaceutically acceptable salt thereof may be formulated for administration by any route, and examples are oral, rectal, topical, parenteral, intravenous or intramuscular administration. Preparations may, if desired, be designed to give slow release of the paroxetine or a pharmaceutically acceptable salt thereof.

The medicaments may, for example, be in the form of tablets, capsules, sachets, vials, powders, granules, lozenges, reconstitutable powders, or liquid preparations, for example solutions or suspensions, or suppositories.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose: or pharmaceutically acceptable setting agents such as sodium lauryl sulphate.

Solid medicaments may be obtained by conventional methods of blending, filling, tabletting or the like. Repeated blending operations may be used to distribute paroxetine or a salt thereof throughout those medicaments employing large quantities of fillers. Then the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing paroxetine or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifing agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Paroxetine or a pharmaceutically acceptable salt thereof may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned hereinbefore, the effective dose of the paroxetine or pharmaceutically acceptable salt depends on the severity of the disorders, the condition of the patient and on the frequency and route of administration. A unit dose will generally contain from 2 to 1000 mg and preferably will contain from 30 to 500 mg, in particular 10, 20, 30, 40, 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Preferably the unit dose will contain from 10 to 40 mg of paroxetine and be administered in multiples, if desired, to give the preceding daily dose.

The present invention further provides a pharmaceutical composition for use in the treatment and/or prevention of the following depression sub-types: adolescent, bipolar, elderly, major, minor, moderate, recurrent, refractory, severe unipolar, dysthymia, post natal, double depression, post psychotic, post viral, bereavement, primary, secondary, post traumatic stress disorder and depression associated with withdrawal from substances of abuse such as alcohol, nicotine, cocaine, heroin, benzodiazepines, which comprises an effective amount of paroxetine or a pharmaceutically acceptable salt thereof and a pharmaceutically acceptable carrier. Such compositions may be prepared in the manner as hereinbefore described.

The following example demonstrates a suitable pharmaceutical composition:

EXAMPLE 1

The following were mixed together in a conventional manner and compressed into a tablet in a conventional manner.

22.88 mg Paroxetine hydrochloride hemihydrate 244.12 mg Dibasic calcium phosphate dihydrate 15.00 mg Hydroxypropylmethyl cellulose 2910

15.00 mg Sodium starch glycollate 3.00 mg Magnesium Stearate 300.00 mg Total tablet weight

What is claimed is:

1. A method for treating or preventing post traumatic stress disorder, in humans or non-human animals, which method comprises administering an effective amount of paroxetine or a pharmaceutically acceptable salt thereof, to human or non-human animals in need thereof.

2. A method for treating or preventing depression associated with withdrawal from heroin abuse, in humans or non-human animals, which method comprises administering an effective amount of paroxetine or a pharmaceutically acceptable salt thereof, to human or non-human animals in need thereof.

* * * * *

UNITED STATES PATENT AND TRADEMARK OFFICE
CERTIFICATE OF CORRECTION

PATENT NO : 6,121,291

DATED : September 19, 2000

INVENTORS : Maurice Gleeson

It is certified that an error appears in the above-identified patent and that said Letters Patent is hereby corrected as shown below:

On the cover page the inventor's name should read Maurice Gleeson.

Signed and Sealed this

Twenty-fourth Day of April, 2001

*Attest:*

NICHOLAS P. GODICI

*Attesting Officer*     *Acting Director of the United States Patent and Trademark Office*